(12) United States Patent
Hay et al.

(10) Patent No.: US 10,172,908 B2
(45) Date of Patent: Jan. 8, 2019

(54) METHOD FOR TREATING COGNITIVE DYSFUNCTION

(71) Applicant: ARIZONA BOARD OF REGENTS FOR THE UNIVERSITY OF ARIZONA, Tuscon, AZ (US)

(72) Inventors: Meredith Hay, Tuscon, AZ (US); Carol Barnes, Tuscon, AZ (US); John Konhilas, Tuscon, AZ (US)

(73) Assignee: ARIZONA BOARD OF REGENTS FOR THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 14/987,539

(22) Filed: Jan. 4, 2016

(65) Prior Publication Data

US 2016/0206681 A1    Jul. 21, 2016

Related U.S. Application Data (63) Continuation of application No. PCT/US2014/044962, filed on Jun. 30, 2014.

(60) Provisional application No. 61/842,897, filed on Jul. 3, 2013.

(51) Int. Cl.
| | |
|---|---|
| *A61K 38/00* | (2006.01) |
| *A61P 9/12* | (2006.01) |
| *A61K 38/08* | (2006.01) |
| *A61K 9/00* | (2006.01) |
| *A61K 31/381* | (2006.01) |

(52) U.S. Cl.
CPC .......... *A61K 38/085* (2013.01); *A61K 9/0019* (2013.01); *A61K 31/381* (2013.01)

(58) Field of Classification Search
CPC ................................ A61K 38/00; A61K 38/08
See application file for complete search history.

(56) References Cited

U.S. PATENT DOCUMENTS

| | | | |
|---|---|---|---|
| 5,629,292 A | 5/1997 | Rodgers et al. | |
| 5,716,935 A | 2/1998 | Rodgers et al. | |
| 5,834,432 A | 11/1998 | Rodgers et al. | |
| 5,955,430 A | 9/1999 | Rodgers et al. | |
| 6,096,709 A | 8/2000 | Rodgers et al. | |
| 6,110,895 A | 8/2000 | Rodgers et al. | |
| 6,165,978 A | 12/2000 | Rodgers et al. | |
| 6,177,407 B1 | 1/2001 | Rodgers et al. | |
| 6,239,109 B1 | 5/2001 | Rodgers et al. | |
| 6,248,587 B1 | 6/2001 | Rodgers et al. | |
| 6,258,778 B1 | 7/2001 | Rodgers et al. | |
| 6,335,195 B1 | 1/2002 | Rodgers et al. | |
| 6,444,646 B1 | 9/2002 | Rodgers et al. | |
| 6,455,500 B1 | 9/2002 | Rodgers et al. | |
| 6,455,501 B1 | 9/2002 | Rodgers et al. | |
| 6,475,988 B1 | 11/2002 | Rodgers et al. | |
| 6,482,800 B1 | 11/2002 | Rodgers et al. | |
| 6,498,138 B1 | 12/2002 | Rodgers et al. | |
| 6,566,335 B1 | 5/2003 | Rodgers et al. | |
| 6,730,775 B1 | 5/2004 | Rodgers et al. | |
| 6,747,008 B1 | 6/2004 | Rodgers et al. | |
| 6,762,167 B1 | 7/2004 | Rodgers et al. | |
| 6,821,953 B1 | 11/2004 | Rodgers et al. | |
| 6,916,783 B2 | 7/2005 | Rodgers et al. | |
| 7,022,675 B2 | 4/2006 | Rodgers et al. | |
| 7,118,748 B1 | 10/2006 | Rodgers et al. | |
| 7,122,523 B2 | 10/2006 | Rodgers et al. | |
| 7,173,011 B2 | 2/2007 | Rodgers et al. | |
| 7,176,183 B2 | 2/2007 | Rodgers et al. | |
| 7,288,522 B1 | 10/2007 | Rodgers et al. | |
| 7,338,938 B2 | 3/2008 | Rodgers et al. | |
| 7,744,927 B2 | 6/2010 | Rodgers et al. | |
| 8,633,158 B1 | 1/2014 | Franklin | |
| 2008/0312129 A1 | 12/2008 | Souza Dos Santos et al. | |
| 2012/0129776 A1 | 5/2012 | Cohen et al. | |

FOREIGN PATENT DOCUMENTS

| | | |
|---|---|---|
| CA | 2 613 126 A1 | 1/2007 |
| JP | 2011-500677 A | 1/2011 |
| JP | 2013-047249 A | 3/2013 |
| WO | WO 02/06308 A2 | 1/2002 |
| WO | WO 2009/114461 A2 | 9/2009 |
| WO | WO 2012/021578 A1 | 2/2012 |
| WO | WO 2012/070936 A | 5/2012 |

(Continued)

OTHER PUBLICATIONS

Veronese et al., www.drugdiscoverytoday.com, vol. 10, No. 21, Nov. 2005.*
New York Times, available online at: https://web.archive.org/web/20131214023401/http://www.nytimes.com/health/guides/symptoms/memory-loss/overview.html, accessed on Jun. 29, 2017.*
UCSF Medical Center, Memory Disorders, available online at: https://www.ucsfhealth.org/conditions/memory_disorders/, accessed on Jun. 29, 2017.*
Megget, Breaking News on Global Pharmaceutical Technology & Manufacturing, Add PEG to make the drug go farther, Nov. 8, 2007.*
National Heart, Lung, and Blood Institute, Heart Failure Also known as Congestive heart failure, available online at https://www.nhlbi.nih.gov/print/4955, accessed on Feb. 7, 2018.*
Canadian Office Action, Canadian Patent Application No. 2,916,701, dated Jul. 5, 2016.
Patent Examination Report No. 1, Patent Application No. 2014284496, dated Jul. 25, 2016.

(Continued)

*Primary Examiner* — Rachael E Bredefeld
*Assistant Examiner* — Kaipeen E Yang
(74) *Attorney, Agent, or Firm* — Anthony C. Kuhlmann; One LLP (57) ABSTRACT

The present invention provides compositions and methods for treating cognitive impairment or dysfunction in a subject. In particular, the present invention provides a method for using a composition comprising an angiotensin-(1-7) receptor agonist to treat cognitive dysfunction or impairment that is due to a various clinical conditions including, but not limited to, those associated with increase in inflammation, cytokine production, increases in reactive oxygen species, changes in expression of brain inflammatory related genes and/or in the expression of genes involved in learning and memory within the central nervous system of a subject.

5 Claims, 3 Drawing Sheets

Specification includes a Sequence Listing.

(56) References Cited

FOREIGN PATENT DOCUMENTS

| WO | WO 2013/090833 A1 | 6/2013 |
|----|----|----|
| WO | WO 2013/119870 A1 | 8/2013 |
| WO | WO 2013/172956 A1 | 11/2013 |
| WO | WO 2014/021942 A1 | 2/2014 |
| WO | WO 2014/055591 A1 | 4/2014 |
| WO | WO 2014/116587 A1 | 7/2014 |
| WO | WO 2014/151338 A1 | 9/2014 |
| WO | WO 2014/179440 A1 | 11/2014 |
| WO | WO 2016/112247 A1 | 7/2016 |

OTHER PUBLICATIONS

Hellner et al., "Angiotension-(1-7) enchances LTP in the hippocampus through the G-protein-coupled receptor Mas", Molecular and Cellular Neuroscience, Jul. 1, 2005, pp. 427-435, vol. 29, issue 3.
Fontes et al., "Evidence that angiotensin-(1-7) plays a role in the central control of blood pressure at the ventro-lateral medulla acting through specific receptors", Brain Research, Nov. 28, 1994, pp. 175-180, vol. 66, issue 1.
International Search Report and Written Opinion, PCT/US2014/044962, dated Nov. 18, 2014.
Japanese Office Action, Application No. 2016-524300, dated Nov. 1, 2016.
Extended European Search Report, Application No. 14820282.3, dated Dec. 16, 2016.
Albrecht, "Angiotensin-(1-7)-induced plasticity changes in the lateral amygdala are mediated by COX-2 and NO", Learning and Memory, vol. 14, No. 3 (Mar. 2007) pp. 177-184.
Bodiga, et al., "Renin Angiotensin System in Cognitive Function and Dementia," Asian J. of Neurosci, vol. 19, No. 10 (2013) pp, 3952-3962.
Ciobica, et al., "Brain renin-angiotensin system in cognitive function: pre-clinical findings and implications for prevention and treatment of dementia", ACTA Neural. Belg., vol. 109 (Jan. 2009) pp. 171-180.
Ciobica, et al., "The Effects of Angiotensin II and Angiotensin 1-7 in Cognitive Processes and Oxidative Stress in Rates, Relevance for Alzheimer's Disease", Alzheimer's & Dementia: The Journal of the Alzheimer's Association, vol. 7, No. 4 (Jul. 2011) pp. S112-S113.
Fontes, et al., "Evidence that angiotensin-(1-7) plays a role in central control of blood pressure at the ventro-lateral medulla acting through specific receptors," Brain Research, vol. 665 (Nov. 1994) pp. 175-180.
Hellner, et al., "Angiotensin-(1-7) enhances LTP in the hippocampus through the G-Protein-coupled receptor Mas", Mol. Cell. Neurosoi, Vol, 29, No. 3 (Jul. 2005) pp. 427-435.
Jiang, et al., "ACE2-Ang-(1-7)-Mas Axis in Brain: A Potential Target for Prevention and Treatment of Ischemic Stroke," Current Neuropharmacology, (Jan. 2013) pp. 209-217.
Lazaroni, et al., "Angiotensin-(1-7)/Mas axis integrity is required for the expression of object recognition memory," Neurobiology of Learning & Memory, vol. 97, No. 1 (Oct. 2011) 113-123, San Diego, CA, US.
Passos-Silva, et al., "Angiotensin-(1-7): beyond the cardio-renal actions," Clin. Sci., vol. 124, (2013) pp. 443-456, Great Britain.
Silva, et al., "Promising Neuroprotective Effects of the Angiotensin 1-7/ACE2/Mas axis in Stroke", Exp. Physiol. vol. 99, No. 2 (Feb. 2014) pp. 342-343.
Xie, et al., "Angiotensin-(1-7) improves cognitive function in rats with chronic cerebral hypoPerfusion," Brain Research, vol. 1573 (May 2014) pp. 44-53.
Xu, et al., "ACE2/ANG-(1-7)/Mas pathway in the brain: the axis of good," Am. J. Physiol. Regul. Integra Comp. Physiol., vol. 300 (Dec. 2010) pp. R804-R817.

* cited by examiner

METHOD FOR TREATING COGNITIVE DYSFUNCTION

CROSS-REFERENCE TO RELATED APPLICATIONS

This application is a continuation of, and claims the priority benefit of, application PCT/US2014/044962 filed on Jun. 30, 2014, which claims the priority benefit of U.S. Provisional Application No. 61/842,897 filed Jul. 3, 2013, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 21, 2016, is named 33032.4011_SL.txt and is 1,859 bytes in size.

FIELD OF THE INVENTION

The present invention relates to compositions and methods for the treatment of cognitive impairment or dysfunction. In particular, the present invention relates to the use of angiotensin-(1-7) receptor agonist to treat cognitive dysfunction.

BACKGROUND OF THE INVENTION

Cognitive dysfunction or impairment is a common neurological complication of congestive heart failure ("CHF") and post cardiac surgery affecting approximately 50-70% of patients at hospital discharge and 20-40% of patients six months after surgery. The occurrence of CHF and postoperative cognitive dysfunction is associated with increased duration of hospitalization and impaired long-term quality of life. Without being bound by any theory, it is believed that in general any clinical condition associated with an increase in inflammatory cytokines and/or increase in reactive oxygen species in central nervous system, in particular in the brain, can lead to cognitive dysfunction.

Unfortunately, there is no effective pharmacological treatment for cognitive impairment or dysfunction for CHF and postoperative patients or for any other clinical condition associated with an increase in inflammation cytokines and/or increase in reactive oxygen species in the brain.

Accordingly, there is a need for a treatment for cognitive dysfunction in a clinical condition associated with an increase in inflammatory cytokines and/or increase in reactive oxygen species.

SUMMARY OF THE INVENTION

One particular aspect of the invention relates to compositions and methods for treating cognitive dysfunction by administering an angiotensin-(1-7) receptor agonist. Compositions and methods of the invention can be used to treat cognitive impairment or dysfunction (1) associated with pre- and/or post-surgery dementia, or (2) observed in patients with congestive heart failure (CHF), cardiovascular disease, or hypertension. As used herein, the terms "treating" and "treatment" of cognitive dysfunction or impairment refer to: (1) preventing cognitive dysfunction from occurring, i.e., causing the clinical symptoms of cognitive dysfunction not to develop in a subject that may be or predisposed to developing cognitive dysfunction or impairment but does not yet experience or display symptoms of cognitive dysfunction or impairment; (2) inhibiting cognitive dysfunction of impairment, i.e., arresting or reducing the development of cognitive dysfunction or impairment or its clinical symptoms; or (3) relieving cognitive dysfunction or impairment, i.e., causing regression of cognitive dysfunction or impairment or its clinical symptoms.

More generally, compositions and methods of the invention are useful in treating cognitive dysfunction or impairment in a subject whose cognitive dysfunction or impairment is clinically associated with an increase in inflammatory cytokines and/or increase in reactive oxygen species in the central nervous system, in particular the brain. As used herein, the term "clinically associated" refers to the root cause or underlying cause of cognitive dysfunction or any other clinical condition that when ameliorated results in reduction, prevention, treatment or reversal of cognitive dysfunction. Exemplary clinical conditions associated with an increase in inflammatory cytokines and/or increase in reactive oxygen species that can cause cognitive dysfunction or impairment include, but are not limited to, circulatory compromise, cardiovascular disease, hypertension, hypotension, congestive heart failure, stroke, embolism, surgery (e.g., postoperative recovery condition), dementia, Alzheimer's disease, disease related cognitive impairment, trauma related cognitive impairment, age-related dementia, postoperative related delirium and/or increase in inflammatory cytokine and/or increase in reactive oxygen species within the central nervous system of said subject or a combination thereof.

In some embodiments, the composition of the invention includes a peptidic angiotensin-(1-7) receptor agonist, a non-peptidic angiotensin-(1-7) receptor agonist, or a mixture thereof. In one particular instance, the composition of the invention comprises angiotensin-(1-7) (i.e., "Ang-(1-7)") peptide or a derivative thereof. "A derivative" of Ang-(1-7) refers to a homolog or an analog of Ang-(1-7). Exemplary derivatives of Ang-(1-7) include, but are not limited to:

(i) peptides derived from Ang-(1-7);
(ii) peptides in which one or several amino acids of the natural Ang-(1-7) sequence have been substituted by other amino acids;
(iii) Ang-(1-7) modified at the N- and/or C-terminal end of the peptide sequence, for example, by substitution; thus, esters and amides can be considered as C-terminal derivatives;
(iv) Ang-(1-7) peptides the modification of which prevents their destruction by proteases or peptidases, as well as to peptide-PEG-conjugates derived from the basic sequence of Ang-(1-7);
(v) modified peptides which are derived from the chain of Ang-(1-7) and wherein one or several of the amino acids of the sequence have been substituted by genetically encoded or not genetically encoded amino acids or peptidomimetics. They may exist as free peptides or as C-terminal derivative and/or being linked to a polyethylene glycol (PEG)-polymer, and have the desired Ang-(1-7) effects, i.e., are angiotensin-(1-7) receptor agonists;
(vi) peptides having conservative substitutions of amino acids as compared to the natural sequence of Ang-(1-7) in one or several positions. A conservative substitution is defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysins, arginins, histidine), acidic side chains (aspartic acid, glutamic acid), uncharged polar side chains (glycine, aspartamic acid, glutamine, serine, threonine, tyrosine, cysteine), non-polar side chains (alanine, valine, leucine, isoleucine, proline, phenylalanine, methionine, tryptophan), β-branched side chains (threonine, valine, isoleucine) and aromatic side chains (tyrosine, phenylalanine, tryptophane, histidine). Such conservative substitutions of side chains are typically carried out in non-essential positions. In this context, an essential position in the sequence is one wherein the side chain of the relevant amino acid is of significance for its biological effect.

Non-peptidic Ang-(1-7) receptor agonists as well as other peptidic angiotensin-(1-7) receptor agonists are known to one skilled in the art or can readily be identified using any one of the known assay methods. See, for example, U.S. Pat. Nos. 6,984,660; and 8,383,772, PCT Patent Publication Nos. WO 2009100513; WO 2013010241; WO 2006128266; WO 2010009524; and WO 02072569, all of which are incorporated herein by reference in their entirety.

In one particular aspect of the invention, a method is provided for treating cognitive dysfunction and/or memory loss due to a clinical condition associated with increase in inflammation, cytokine production, increases in reactive oxygen species, changes in expression of brain inflammatory related genes and/or in the expression of genes involved in learning and memory within the central nervous system of a subject. Such method includes administering a therapeutically effective amount of an angiotensin-(1-7) receptor agonist to said subject in need of such a treatment to treat cognitive dysfunction and/or memory loss. As used herein, "a therapeutically effective amount" means the amount of a compound or a composition that, when administered to a subject to treat cognitive dysfunction and/or memory loss, is sufficient to effect such treatment for cognitive dysfunction and/or memory loss. The "therapeutically effective amount" will vary depending on the compound or the composition, and the severity of cognitive dysfunction and/or memory loss, and the age, weight, etc., of the subject to be treated.

In some embodiments, said angiotensin-(1-7) receptor agonist is an angiotensin-(1-7) Mas receptor agonist.

Yet in other embodiments, said clinical condition comprises circulatory compromise, cardiovascular disease, hypertension, hypotension, congestive heart failure, stroke, embolism, surgery (e.g., postoperative recovery condition), dementia, Alzheimer's disease, disease related cognitive impairment, trauma related cognitive impairment, age-related dementia, postoperative related delirium and/or increase in inflammatory cytokine and/or increase in reactive oxygen species within the central nervous system of said subject or a combination thereof.

Still in other embodiments, said angiotensin-(1-7) receptor agonist comprises a peptidic angiotensin-(1-7) receptor agonist, a non-peptidic angiotensin-(1-7) receptor agonist, or a combination thereof.

In other embodiments, said angiotensin-(1-7) receptor agonist comprises angiotensin-(1-7) or a derivative thereof.

BRIEF DESCRIPTION OF THE DRAWINGS

FIG. 1 shows the effects of Ang-(1-7) systemic administration on object recognition impairment observed following 8 weeks of congestive heart failure. Mice were 12 weeks post MI or sham surgery. Six mice were MI+Ang(1-7); three mice were MI+saline; and four mice were Sham+Ang (1-7). Alzet pumps with either Ang(1-7) or saline were implanted sq 3 weeks prior to NOR test. Novel object recognition test was performed 3 weeks post pump implant. Data shown are 1st 2 min of "test phase" DRatio=(t novel−t familiar)/(t novel+t familiar). A positive score indicates more time spent with the novel object, a negative score indicates more time spent with the familiar object, and a zero score indicates a null preference. *=p<0.05, #=p<0.05. ANOVA+posthoc Turkey test.

DETAILED DESCRIPTION OF THE INVENTION

Some aspects of the invention are based on the discovery by the present inventors that cognitive dysfunction and/or memory loss can be treated by administering Ang-(1-7) receptor agonist. In particular, the present inventors have discovered that in a mouse model of CHF induced cognitive decline, administration of Ang-(1-7) rescued the cognitive impairment post 12 weeks after myocardial infarction (MI).

Angiotensin-(1-7) is an endogenous peptide, some of which are derived from Angiotensin II conversion via angiotensin converting enzyme 2 (ACE2), and from angiotensin I by a number of peptidases. Ang-(1-7) are known inter alia to activate Mas receptor. Increases in circulating Ang-(1-7) has been reported to increase in patients and animal models following administration of ACE inhibitors due to the increase in Angiotensin I which results in increased Angiotensin I conversion to Ang-(1-7). Ang-(1-7) has been shown to decrease inflammation and oxidative stress in both the heart and brain in preclinical studies.

Cognitive dysfunction is a common neurological complication of a wide variety of clinical conditions including, but not limited to, congestive heart failure and post cardiac surgery. The occurrence of CHF and postoperative cognitive dysfunction is associated with increased duration of hospitalization and impaired long-term quality of life.

Renin Angiotensin System: Aging, Heart Failure and Cognitive Function:

Some studies have shown that elderly patients in heart failure and hypertension are known to have hospital readmission rates ranging from 40 to 50% within 6 months. It has been suggested that the high readmission rates are due, at least in part, to patient's non-compliance with therapy due to increased cognitive impairment. The incidence of cognitive impairment is particularly high in cardiovascular disease and congestive heart failure patients with 30% to 80% of patients being diagnosed with some degree of cognitive loss. To date, there is no known therapy for the prevention or treatment of postoperative cognitive dysfunction or impairment or cognitive dysfunction or impairment due to a clinical condition associated with cardiovascular disease and congestive heart failure as well as other clinical conditions described above.

Recently, there has been considerable attention paid to the role of ACE1 blockers and AngII in age changes in memory, cardiovascular disease and congestive heart failure, Alzheimer's disease and dementia. Studies in elderly cardiovascular disease and congestive heart failure and in essentially hypertensive patients found that treatment with ACE inhibitors improved cognitive function independent of the effect on blood pressure. The mechanisms underlying these effects are thought to include decreases in brain AngII, which would decrease the known deleterious inflammatory effects of AngII on memory and hippocampus function. In addition, a decrease in AngII would attenuate AngII inhibition of acetylcholine release. In addition, it was believed by others that decrease in AngII would also increase availability of AngI conversion to Ang(1-9) and Ang-(1-7) ultimately to form Ang(2-7) and Ang(3-7) thus increasing activation of AT4 receptors, which are known to facilitate hippocampus LTP.

Ang-(1-7) and the Brain:

Recently, it has become recognized that RAS involves two separate enzymatic pathways that provide a physiological counterbalance of two related peptides acting at distinct receptors. The well described ACE-AngII-AT1R system is thought to be physiologically opposed and balanced by the ACE2-Ang-(1-7)-Mas receptor system. In the brain and other tissues, AngII activation of AT1 receptors increases reactive oxygen species ("ROS") and inflammation while Ang-(1-7) and Mas receptor activation decrease ROS and inflammation. The role of ACE2 in the modulation of central brain function has been shown to inhibit central AngII induced hypertension by increasing Ang-(1-7) activation of the Mas receptor, increase NO release and, in endothelial cells, decrease ROS formation.

As discussed above, some of the Ang-(1-7) are produced from ACE2 cleavage of AngII. Ang-(1-7) has been shown to increase NO in the brain via activation of both the Mas receptor and AT2R. Further, over expression of ACE2 in the paraventricular nucleus of ACE2 knockout mice, reduced Ang II mediated oxidative stress. In the kidney, Ang-(1-7) activation of Mas receptors has been shown to directly increase intracellular NO and attenuated Ang II activation of ROS. In addition, it has been shown that in older animals, there is a marked reduction of kidney ACE2 function and a loss of Ang-(1-7) compared to younger animals. The role of reactive oxygen species in age related changes in learning and memory have been extensively studied. In younger healthy animals, ROS and NADPH appear to be required for normal learning and hippocampal LTP; however, in aging animals, LTP and memory impairments were shown to be linked to increased ROS.

The hippocampus is also known to express ACE 2 and the Ang-(1-7) Mas receptor. Recent studies in mice lacking the Mas receptor have shown that Ang-(1-7) and the Mas receptor are important for normal object recognition processing and blockade of the Mas receptor in the hippocampus impairs object recognition. Earlier studies have shown that Ang-(1-7) facilitates LTP in CA1 cells and this effect is blocked by antagonism of the Mas receptor. To date, no studies have been conducted to determine the role of ACE2 in cognition and its changes during aging. Furthermore, the cellular mechanisms regarding the hippocampus ACE2/Ang-(1-7)/Mas receptor axis is currently unknown.

In one particular aspect of the invention, a method is provided for treating cognitive dysfunction and/or memory loss in a subject. Such a method includes administering a therapeutically effective amount of an angiotensin-(1-7) receptor agonist to a subject in need of such a treatment.

In some embodiments, said cognitive dysfunction is and/or memory loss is associated with increase in inflammation, cytokine production, increases in reactive oxygen species, changes in expression of brain inflammatory related genes and/or in the expression of genes involved in learning and memory within the central nervous system of the subject.

Yet in other embodiments, said cognitive dysfunction and/or memory loss is associated with cognitive impairment that occur in circulatory compromise, congestive heart failure, postoperative recovery, dementia, Alzheimer's disease, disease related cognitive impairment, and/or trauma related cognitive impairment.

Still in other embodiments, said cognitive dysfunction and/or memory loss is associated with circulatory compromise, cardiovascular disease, hypertension, hypotension, congestive heart failure, stroke, embolism, surgery, dementia, Alzheimer's disease, disease related cognitive impairment, trauma related cognitive impairment, age-related dementia, postoperative related delirium and/or increase in inflammatory cytokine and/or increase in reactive oxygen species within the central nervous system of said subject or a combination thereof.

Exemplary Ang-(1-7) receptor agonists that are useful in the present invention include, but are not limited to, a peptidic angiotensin-(1-7) receptor agonist, a non-peptidic angiotensin-(1-7) receptor agonist, or a mixture thereof. In one particular instance, the composition of the invention comprises angiotensin-(1-7) peptide or a derivative thereof. "A derivative" of Ang-(1-7) refers to a homolog or an analog of Ang-(1-7).

Some aspects of the invention provide compositions comprising an angiotensin-(1-7) receptor agonist that can be used to treat cognitive dysfunction or impairment in a subject. In one embodiment, the present invention provides a composition to inhibit the decline in cognitive function and/or memory in an individual. Compositions and methods of the invention can be used to prevent or even reverse decline in cognitive ability.

In one particular embodiment, a method is provided for improving cognitive function, learning and memory or protecting from loss of cognitive function known to occur in a subject or patient following a compromised circulatory function such as congestive heart failure or in post-operative patients. As shown in the Examples section using an appropriate animal model, the present inventors have discovered that administration of a therapeutically effective amount of angiotensin-(1-7) or angiotensin-(1-7) receptor agonist improves cognitive function, learning and memory or protects from loss of cognitive function known to occur in following a compromised circulatory function such as congestive heart failure or in post-operative patients.

Administration of a therapeutically effective amount of ang-(1-7) receptor agonist increases the expression of genes involved in learning and memory, improves cerebrovascular function, and/or decreases expression of brain inflammatory related genes. Thus, some embodiments of the invention provide a method for increasing the expression of a gene involved in learning and memory or improving cerebrovascular function or decreasing the expression of a brain inflammatory related gene by administering a therapeutically effective amount of Ang-(1-7) receptor agonist to a subject.

In some aspects, the present invention provides a treatment for the prevention of cognitive dysfunction or impairment and/or improvement in cognitive function that is associated with clinical conditions described herein including, but not limited to, cardiovascular disease, congestive heart failure and postoperative related decline in cognitive function. In some embodiments, the invention provides a method for treating cognitive dysfunction or impairment by administering a therapeutically effective amount of an Ang-(1-7) receptor agonist. In some instances, the Ang-(1-7) receptor agonist selectively targets the brain tissue, often with high efficacy, to either reduce cellular signals that promote cognitive impairment or to increase cellular signals that promote cognitive function.

In other embodiments, the Ang-(1-7) receptor agonist is Ang-(1-7) peptide or a derivative thereof.

Still in other embodiments, the composition comprises a compound that increases plasma, tissue or cellular Ang-(1-7) level.

Yet in other embodiments, the composition comprises a compound that inhibits or reduces neuronal reactive oxygen species production and/or NAD(P)H related enzyme expression.

In one particular embodiment, the angiotensin-(1-7) receptor agonist comprises angiotensin-(1-7) peptide.

Administration and Pharmaceutical Composition:

The present invention includes pharmaceutical compositions comprising at least one Ang-(1-7) receptor agonist or a pharmaceutically acceptable salt or solvate thereof, together with at least one pharmaceutically acceptable carrier, and optionally other therapeutic and/or prophylactic ingredients.

In general, the composition of the invention is administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors, e.g., the severity of the cognitive impairment, the age and relative health of the subject, the potency of the Ang-(1-7) receptor agonist used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compositions of the invention are administered as pharmaceutical formulations including those suitable for oral (including buccal and sub-lingual), nasal, pulmonary or parenteral (including intramuscular, intraarterial, intrathecal, subcutaneous and intravenous) administration or in a form suitable for administration by inhalation or insufflation. Typical manner of administration is generally oral or parenteral using a convenient dosage regimen which can be adjusted according to the degree of affliction.

Compositions of the invention can include one or more conventional adjuvants, carriers, or diluents, and can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of sterile injectable solutions for parenteral use. Formulations containing about 100 milligram of active ingredient or, more broadly, about 1 to about 1,000 milligrams, per tablet, are accordingly suitable representative unit dosage forms.

The compositions of the invention can be formulated in a wide variety of oral administration dosage forms. The pharmaceutical compositions and dosage forms can comprise an Ang-(1-7) receptor agonist or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

Ang-(1-7) receptor agonists can also be formulated for parenteral administration (e.g., by injection, for example bolus injection or continuous infusion) and can be presented in unit dose form in ampoules, pre-filled syringes, small volume infusion or in multi-dose containers with an added preservative. The compositions of the invention can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compositions of the invention can also be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compositions of the invention can be formulated for aerosol administration, particularly to the respiratory tract and including intranasal administration. The compositions will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of Ang-(1-7) receptor agonist can be controlled by a metered valve. Alternatively the active ingredients can be provided in a form of a dry powder, for example, a powder mix of the composition in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compositions of the invention can be formulated in transdermal or subcutaneous drug delivery devices. These delivery systems are advantageous when sustained release of the ang-(1-7) receptor agonist is necessary or desired and when patient compliance with a treatment regimen is crucial. Compositions in transdermal delivery systems are frequently attached to a skin-adhesive solid support. The compositions of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of ang-(1-7) receptor agonist. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

Examples

Figure 1:
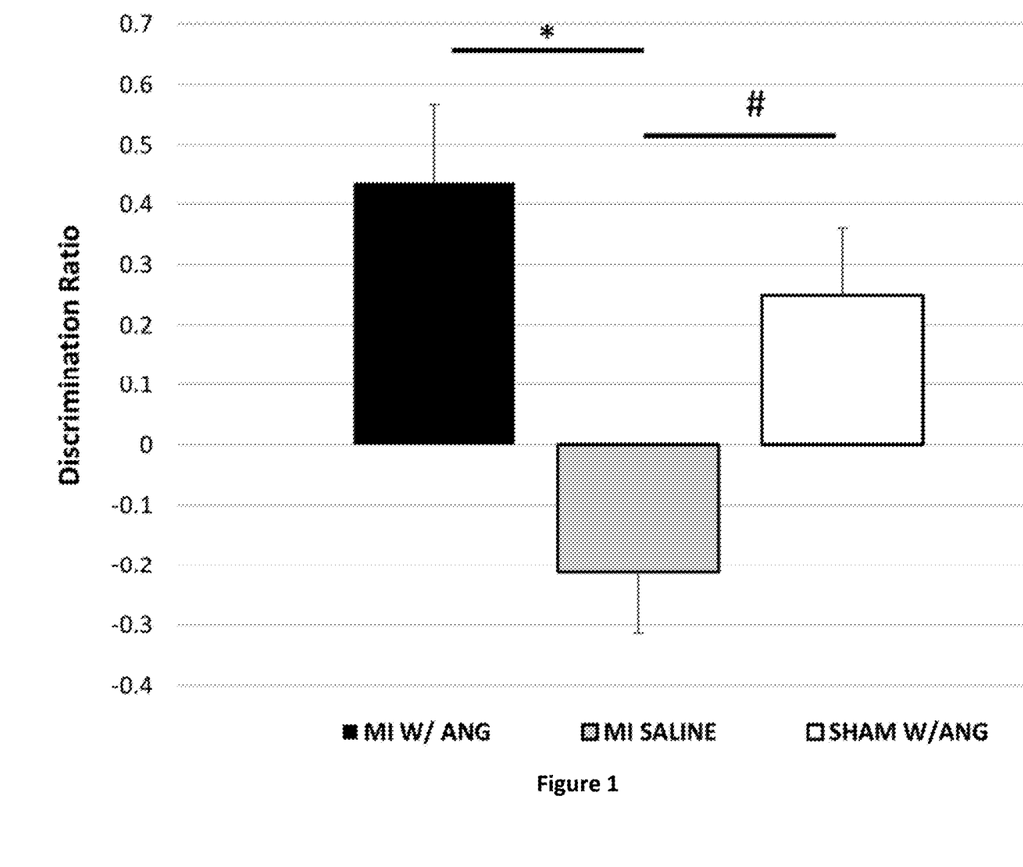

Ang-(1-7) Reverses Congestive Heart Failure Reduction in Object Recognition Memory:

FIG. 1 shows the effects of systemically administered Ang-(1-7) on object recognition impairment following 8 weeks of congestive heart failure. Myocardial infarction and subsequent CHF was induced by ligation of the left coronary artery. By week 4 and week 8 post MI, CHF mice (n=15) had approximately 50 and 70% decline in ejection fraction as measured by echocardiography. For the object recognition SOR test at 8 weeks post MI, discrimination ratios were calculated from the time spent exploring the novel versus familiar object during the test phase. The CHF mice (n=5) had significantly lower discrimination ratios compared to the shams (−0.43+0.05 vs +0.16±0.1, $F(1.7)=27.4$, $p=0.001$, ANOVA). At 8 weeks post MI, a subgroup of CHF mice (n=6) and controls (n=4) were given 50 mcg/kg/hr Angiotensin (1-7) or saline subcutaneously for 4 weeks and then cognitive function was retested. Following 3 weeks of treatment with systemic Ang-(1-7), SOR discrimination ratios for CHF mice (n=6) were similar to controls (n=3) (+0.43±0.1 vs +0.25±0.2) but were significantly different to the CHF mice treated with saline (n=4, −0.21±0.1, $F(2.10)=6.0$, $p=0.01$, ANOVA).

Figure 2:
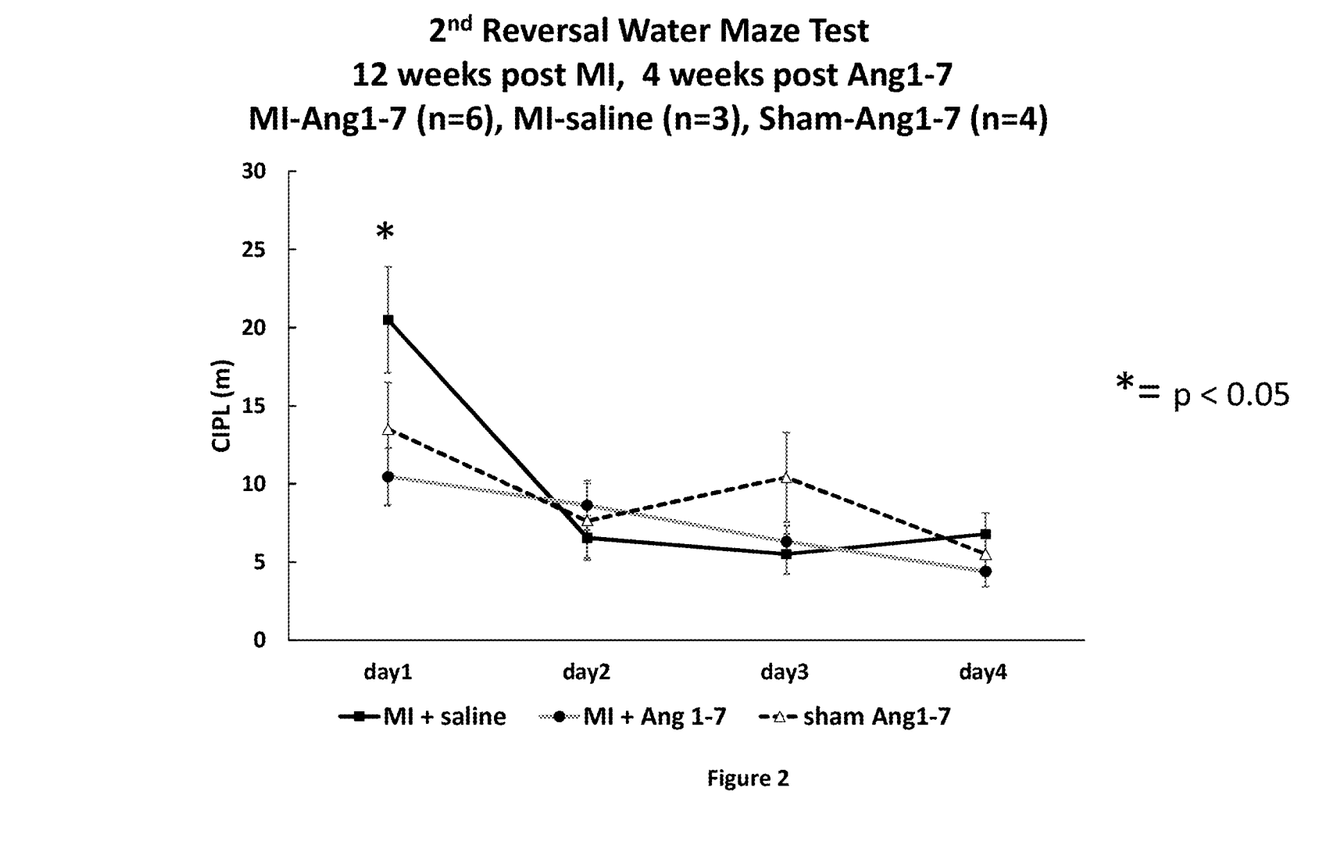
FIG. 2 shows the effects of Ang-(1-7) systemic administration on spatial memory as tested by the Morris water maze task.

Ang-(1-7) Reverses Congestive Heart Failure Reduction in Spatial Memory:

FIG. 2 shows the effects of systemic administration of Ang-(1-7) on spatial memory as tested by the Morris water maze task. Prior to MI, the controls and CHF mice groups performed similarly on the Morris water task. Myocardial infarction and subsequent CHF was induced by ligation of the left coronary artery. By week 4 and week 8 post MI, CHF mice had approximately 50 and 70% decline in ejection fraction as measured by echocardiography. At both 4 (n=10) and 8 weeks (n=9) post MI, the mean performance of the CHF mice in the Morris water task was significantly worse than the performance of the controls (n=4). Animals were tested over 4 days with 6 spatial trials per day. The corrected integrated path length (CIPL) at both 4 and 8 weeks post MI was significantly decreased on day 4 (−66.9±1.6%, −65.3±1.1% respectively, compared to control, ($F(1.75)=9.11$, $p=0.003$, ANOVA, 4 week post MI). At 8 weeks post MI, a subgroup of CHF mice (n=6) and controls (n=4) were given 50 mcg/kg/hr Angiotensin (1-7) or saline subcutaneously for 4 weeks and then cognitive function was retested. Mice receiving Ang-(1-7) showed a significant improvement on object recognition memory on the first day of testing.

Figure 3:
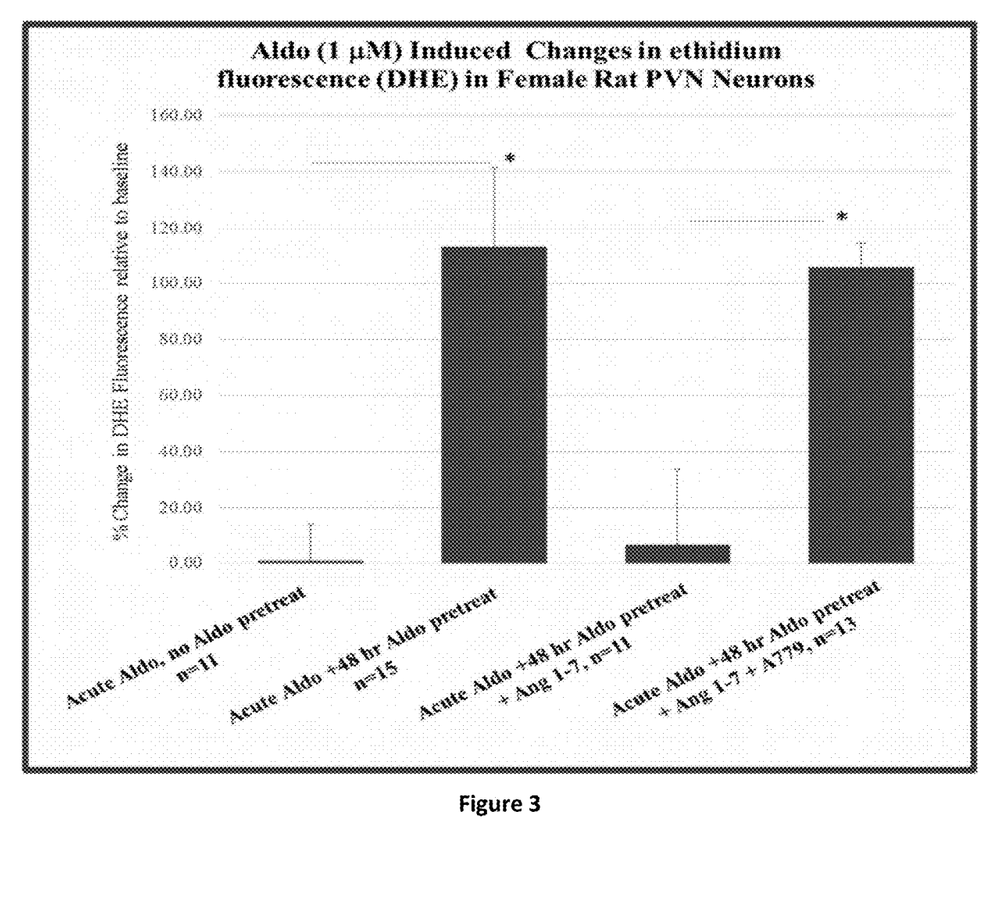
FIG. 3 shows the summary effects of 1 μM Ang-(1-7) inhibition of reactive oxygen production in neurons.

Ang-(1-7) Inhibits Production of Reactive Oxygen in Neurons:

FIG. 3 shows the summary effects of 1 µM Ang-(1-7) inhibition of reactive oxygen species production in neurons. Paraventricular neurons were isolated from 22 day old female SD rats, dissociated and cultured on round coverslips and maintained in HBSS media for at least 48 hours prior to visualization by confocal microscopy. All cells were pre-incubated in 10 nM ALDO for 48 hours and then 1.0 µM Ang-(1-7) or 1.0 µM Ang-(1-7)+10.0 µM A779 for 2 hours prior to testing with acute 1.0 µM Aldo. To measure ROS, changes in the ethidium fluorescence were measured which is directly proportional to the oxidation of dihydroethidium (DHE) by ROS. The cells were loaded with DHE (20 µM) added to the cell culture media for 1 h and then placed in a chamber for microscopic visualization of fluorescence. Oneway ANOVAs for the experimental groups response to acute Aldo was determined. After establishing a significant ANOVA, post-hoc analyses were performed with Tukey multiple comparison tests between pairs of mean change scores. All data are expressed as means±SE. Statistical significance was set at $P<0.05$.

Perfusion with 1.0 µM ALDO increased ROS (D=113.4+28%) in the PVN neurons. In cells pre-incubated in Ang-(1-7), ALDO increase in ROS was significantly inhibited (D=6.4+27%). Pre-incubation in Ang-(1-7)+A779, restored the ALDO increase in ROS (Delta=105.9+9%). Change in ROS production was standardized relative to control state prior to ALDO treatment during ACSF incubation. ANOVA followed by Tukey's post hoc test was used for statistical comparisons between control and ALDO treatment. Differences were considered statistically significant when $p\leq0.05$. * indicates $p\leq0.05$.

Patients with congestive heart failure or cardiovascular disease have a much higher probability of mortality if they are concomitantly diagnosed with cognitive decline and memory loss. Furthermore, these patients have hospital readmission rates ranging from 40 to 50% within 6 months that are due, in part, to patient's non-compliance with therapy as a result of cognitive impairment. As discussed herein, compositions and methods of the invention are useful in treating cognitive dysfunction or impairment associated with a variety of clinical conditions discussed herein.

In addition, the invention provides a preclinical animal model of cardiovascular disease and congestive heart failure induced cognitive dysfunction. A total of 26, male C57Bl/6J mice were randomly assigned to the control group or cardiovascular disease and congestive heart failure group. Myocardial infarction was induced by ligation of the left coronary artery. By week 4 and week 8 post MI, cardiovascular disease and congestive heart failure mice (n=15) had approximately 50 and 70% decline in ejection fraction as measured by echocardiography. Mice were tested for changes in spatial learning memory via the Morris water task and object recognition via the standard spontaneous object recognition (SOR) task at 4 and 8 weeks post MI. At 8 weeks post MI, a subgroup of cardiovascular disease and congestive heart failure mice (n=6) and the control mice (n=4) were given 50 mcg/kg/hr Angiotensin (1-7) or saline subcutaneously for 4 weeks and then cognitive function was retested.

Prior to MI, the control mice and cardiovascular disease and congestive heart failure mice groups performed similarly on the Morris water task. At both 4 (n=10) and 8 weeks (n=9) post MI, the mean performance of the cardiovascular disease and congestive heart failure mice in the Morris water task was significantly worse than the performance of the control mice (n=4). Animals were tested over 4 days with 6 spatial trials per day. The corrected integrated path length (CIPL) at both 4 and 8 weeks post MI was significantly decreased on day 4 (−66.9±1.6%, −65.3±1.1% respectively, compared to control, (F (1.75)=9.11, p=0.003, ANOVA, 4 week post MI). For the object recognition SOR test at 8 weeks post MI, when discrimination ratios were calculated from the time spent exploring the novel versus familiar object during the test phase, the cardiovascular disease and congestive heart failure mice (n=5) had significantly lower discrimination ratios compared to the control mice (−0.43+0.05 vs +0.16±0.1, F(1.7)=27.4, p=0.001, ANOVA). Following 3 weeks treatment with systemic Ang-(1-7), cardiovascular disease and congestive heart failure mice (n=6) SOR discrimination ratios were similar to the control mice (n=3) (+0.43±0.1 vs +0.25±0.2) and significantly different compared to the cardiovascular disease and congestive heart failure mice treated with saline (n=4, 0.21±0.1, F (2.10)=6.0, p=0.01, ANOVA). Interestingly, ejection fraction was not significantly impacted by Ang-(1-7) treatment. These results show that the preclinical mouse model of cardiovascular disease and congestive heart failure exhibit both spatial memory and object recognition dysfunction and that this cognitive dysfunction is attenuated by treatment with systemic Ang-(1-7). (JK R01HL098256, KO2HL105799, C B McKnight Brain Research Foundation). Angiotensin (1-7) and Mas receptor activation inhibit Aldosterone induced ROS inflammatory responses in neurons of the paraventricular nucleus (PVN).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating cognitive impairment caused by brain inflammation in a subject comprising systemically administering to the subject a therapeutically effective amount of angiotensin-(1-7) or a derivative of angiotensin-(1-7) selected from the group consisting of:

```
Asp-Arg-Val-Ser-Ile-His-Pro,      (SEQ ID NO: 1)

Asp-Arg-Val-Tyr-Ile-His-Cys,      (SEQ ID NO: 2)

Asp-Arg-Val-Ser-Ile-His-Cys,      (SEQ ID NO: 3)

Asp-Arg-NorLeu-Tyr-Ile-His-Pro,   (SEQ ID NO: 4)

Arg-Val-Tyr-Ile-His-Pro-Phe, and  (SEQ ID NO: 6)

Ala-Arg-Val-Tyr-Ile-His-Pro       (SEQ ID NO: 7).
```

2. The method of claim 1, wherein the subject is administered angiotensin-(1-7).

3. The method of claim 2, wherein said angiotensin-(1-7) further comprises a polyethylene glycol polymer.

4. The method of claim 1, wherein said angiotensin(1-7) or derivative of angiotensin-(1-7) is administered by intravenous or subcutaneous injection.

5. The method of claim 1, wherein the angiotensin-(1-7) or the derivative further comprises a polyethylene glycol polymer.

* * * * *

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Asp Arg Val Ser Ile His Pro
1               5

<210> SEQ ID NO 2

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Tyr Ile His Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Arg Val Ser Ile His Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: NorLeu

<400> SEQUENCE: 4

Asp Arg Xaa Tyr Ile His Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Tyr Ile His Pro Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Val Tyr Ile His Pro Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 7

Ala Arg Val Tyr Ile His Pro
1               5
```